United States Patent [19]

Morisawa et al.

[11] Patent Number: 4,487,781

[45] Date of Patent: Dec. 11, 1984

[54] TRIHALOALLYL DERIVATIVES HAVING ANTI-FUNGAL ACTIVITIES

[75] Inventors: Yasuhiro Morisawa; Kiyoshi Konishi; Mitsuru Kataoka, all of Hiromachi, Japan

[73] Assignee: Sankyo Company Limited, Tokyo, Japan

[21] Appl. No.: 410,695

[22] Filed: Aug. 23, 1982

Related U.S. Application Data

[63] Continuation of Ser. No. 166,817, Jul. 8, 1980, abandoned.

[30] Foreign Application Priority Data

Jul. 13, 1979 [JP] Japan .................................. 54-89093
Sep. 14, 1979 [JP] Japan ................................ 54-118118

[51] Int. Cl.³ ........................ A01N 37/14; C07C 69/96
[52] U.S. Cl. .................................. 424/301; 260/463; 560/229; 560/262; 424/311
[58] Field of Search .............. 260/463; 424/301, 314, 424/311; 560/183, 229, 262

[56] References Cited

U.S. PATENT DOCUMENTS 4,259,350  3/1981  Morisawa et al. ................ 560/229

FOREIGN PATENT DOCUMENTS 0015044  of 0000  European Pat. Off. .
19077   11/1966  Japan .
22365    7/1977  Japan .
79862    7/1978  Japan .
116026   7/1982  Japan ................................. 560/262
1376500 12/1974  United Kingdom .
2053916  2/1981  United Kingdom .

OTHER PUBLICATIONS

Unverified Translation of Japanese Patent Publication, 20484/1978 of Kai et al., Supplied by Applicant in Parent Application.

*Primary Examiner*—Anton H. Sutto
*Attorney, Agent, or Firm*—Frishauf, Holtz, Goodman & Woodward

[57] ABSTRACT

1,1,2-Triiodo-1-propene and 1-bromo-1,2-diiodo-1-propene derivatives having a formyloxy, alkanoyloxy, alkoxycarbonyloxy, alkoxycarbonylalkoxy, phenoxycarbonylalkoxy or benzyloxycarbonylalkoxy group at the 3-position are valuable anti-fungal and preservative agents having good heat and light stability.

12 Claims, No Drawings

TRIHALOALLYL DERIVATIVES HAVING ANTI-FUNGAL ACTIVITIES

This is a continuation of application Ser. No. 166,817 filed July 8, 1980, abandoned.

BACKGROUND TO THE INVENTION

The present invention relates to certain new trihaloallyl derivatives, to their use as anti-fungal and preservative agents and to preservative compositions containing them as active ingredients.

Most organic materials are susceptible, to some degree, to attack by a variety of natural pests, especially fungi. Susceptible materials include building materials (such as wood) and industrial materials (such as wet pulp, papers, straw mats, fibres, leathers, adhesives, paints, synthetic resins and, again, wood). The growth of undesirable fungi on these materials can lead not only to contamination but also to structural damage. In the past, reasonably effective control of fungi on such materials has been achieved by the application to these materials of a variety of anti-fungal compounds. The compounds most commonly employed for this purpose are organic compounds of heavy metals (e.g. compounds of lead or tin, particularly tributyltin oxide) or chlorinated phenols (such as pentachlorophenol and its esters). However, these substances are very toxic to humans and other animals and thus not only are they dangerous to handle during application, but they may also give rise to danger during use of any material treated with them. Furthermore, environmental pollution may occur if inadequate safety precautions are taken during treatment of organic materials with these anti-fungal agents or during the use or destruction (e.g. by incineration) of materials treated with them. Accordingly, although these anti-fungal agents have proven of great value in the past, it is anticipated that their future use will be restricted or even banned.

However, the world's diminishing resources make it ever more vital that materials should be adequately preserved. For example, wood preservation has become of increasing importance in recent years due to increasing world demands upon dwinding forest resources and because of the introduction of new building processes (e.g. the prefabricated frame process) and high temperature and humidity conditions in many parts of the world. This demand for preservatives for wood and other organic materials has not been met completely by preservatives of the chlorinated phenol, organotin or inorganic fixing types, since (as explained above) they may be poisonous, or they may be inadequately effective, have an offensive smell and contaminate the material being treated, which makes it difficult to handle the material easily and safely. There is, therefore, a strong demand for new anti-fungal and perservative agents for industrial materials which are more effective, easier to handle and safer.

As a result of this demand, there has recently been some interest shown in halogenated allyl and propargyl derivatives and a number of such derivatives have been discovered, many of them have been proposed for use as anti-fungal, fungicidal or preservative agents. For example, Japanese Patent Publication No. 20484/78 discloses that 2,3,3-triiodoallyl alcohol is useful as an antibacterial and anti-fungal agent for industrial use, whilst Japanese Patent Publication No. 20006/78 discloses that the methyl, ethyl, propyl, and isopropyl ethers of 2,3,3-triiodoallyl alcohol have antibacterial activity. A variety of halogenated propargyl derivatives is disclosed in Japanese Patent Publication Nos. 19077/66 and 33182/74 and in Japanese Kokai (i.e. unexamined Patent Application as laid open to public inspection) No. 22365/79, No. 79862/78, No. 31036/75 and 125614/79; all of these propargyl derivatives have been proposed for use as anti-fungal agents, fungicides or preservative agents.

However, even where these compounds have adequate anti-fungal or preservative activity, many of them tend to have rather low stability to light and heat. This is of considerable importance, since the materials treated with anti-fungal and preservative agents often have to survive for many years and low heat or light stability means that the anti-fungal agent or preservative will degrade and cease to function much before the material which it is supposed to be protecting has finished its useful life.

There is, therefore, a need for anti-fungal and preservative agents for wood and other degradable organic materials which have good weather resistance (especially heat and light resistance) as well as good anti-fungal and preservative activities.

BRIEF SUMMARY OF INVENTION

It is, therefore an object of the present invention to provide a series of new trihaloallyl derivatives useful as preservatives and anti-fungal agents.

It is a further object of the invention to provide a preservative and anti-fungal composition.

It is a still further object of the invention to provide an organic material protected from degradation by means of the trihaloallyl derivatives of the invention.

The trihaloallyl derivatives of the present invention are compounds of formula (I):

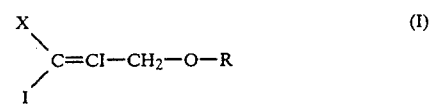

in which:

X represents a bromine atom or an iodine atom, and

R represents a formyl group, an alkanoyl group optionally having one or more halogen substituents, an alkoxycarbonyl group optionally having one or more halogen and/or lower alkoxy and/or halogen-substituted lower alkoxy substituents, an alkoxycarbonylmethyl group, an alkoxycarbonylethyl group, a phenoxycarbonylmethyl group, a phenoxycarbonylethyl group, a benzyloxycarbonylmethyl group or a benzyloxycarbonylethyl group, the phenoxy and benzyloxy groups optionally having one or more halogen and/or lower alkyl substituents in the benzene ring.

DETAILED DESCRIPTION OF INVENTION

One preferred class of compounds according to the present invention are those compounds of formula (Ia):

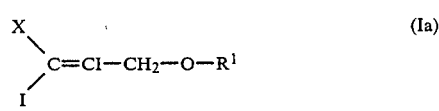

in which:

X is as defined above; and

R¹ represents a formyl group, an alkanoyl group optionally having one or more halogen substituents or an alkoxycarbonyl group optionally having one or more halogen and/or lower alkoxy and/or halogen-substituted lower alkoxy substituents.

Another preferred class of compounds of the present invention are those compounds of formula (Ib):

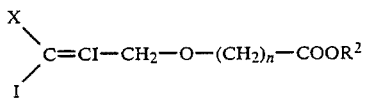

in which:

X is as defined above;

R² represents an alkyl group, a phenyl group optionally having one or more halogen and/or lower alkyl substituents or a benzyl group optionally having one or more halogen and/or lower alkyl substituents in its benzene ring; and n is 1 or 2.

For purposes of the present Specification, the terms "lower alkyl" and "lower alkoxy" mean, respectively, alkyl and alkoxy groups having from 1 to 4 carbon atoms.

Where the groups R in formula (I) and R¹ in formula (Ia) represent alkanoyl groups, these may be straight or branched chain alkanoyl groups and preferably have from 2 to 10 carbon atoms; they optionally have from 1 to 3 halogen substituents. Examples of suitable substituted and unsubstituted alkanoyl groups include the acetyl, propionyl, butyryl, isobutyryl, valeryl, isovaleryl, pivaloyl, 2-methylbutyryl, hexanoyl, 2-methylvaleryl, 2-ethylbutyryl, heptanoyl, octanoyl, 2-ethylhexanoyl, nonanoyl, decanoyl, bromoacetyl, chloroacetyl, dichloroacetyl, trichloroacetyl, 2-bromopropionyl, 3-bromopropionyl, 2-chloropropionyl, 3-chloropropionyl, 2-bromobutyryl, 4-chlorobutyryl, 2-chlorobutyryl, 3-chlorobutyryl, 2-bromoisobutyryl, 2-bromovaleryl, 2-bromoisovaleryl, 2-bromohexanoyl and 2-bromooctanoyl groups.

Where R in formula (I) and R¹ in formula (Ia) represent alkoxycarbonyl groups, these may be straight or branched chain groups and preferably have from 2 to 9 carbon atoms. Where the group is substituted, it preferably has from 1 to 3 substituents chosen from halogen atoms, lower (C₁–C₄) alkoxy groups or lower haloalkoxy groups, preferably having from 2 to 4 carbon atoms. Examples of suitable unsubstituted alkoxycarbonyl groups include the methoxycarbonyl, ethoxycarbonyl, propoxycarbonyl, isopropoxycarbonyl, butoxycarbonyl, isobutoxycarbonyl, sec-butoxycarbonyl, pentyloxycarbonyl, isopentyloxycarbonyl, hexyloxycarbonyl, sec-hexyloxycarbonyl, 2-methylpentyloxycarbonyl, 4-methyl-2-pentyloxycarbonyl, heptyloxycarbonyl and octyloxycarbonyl groups. Where the alkoxycarbonyl group is substituted, it is preferably a straight chain group and more preferably has from 3 to 7 carbon atoms; examples of such groups include the 2-bromoethoxycarbonyl, 2-chloroethoxycarbonyl, 2-iodoethoxycarbonyl, 2-fluoroethoxycarbonyl, 2,2-dichloroethoxycarbonyl, 2,2,2-trichloroethoxycarbonyl, 3-chloropropoxycarbonyl, 3-bromopropoxycarbonyl, 1-bromo-2-propoxycarbonyl, 1-chloro-2-propoxycarbonyl, 2,3-dibromopropoxycarbonyl, 2,3-dichloropropoxycarbonyl, 4-chlorobutoxycarbonyl, 6-chlorohexyloxycarbonyl, 2-methoxyethoxycarbonyl, 2-ethoxyethoxycarbonyl, 2-(2-chloroethoxy)ethoxycarbonyl and 2-butoxyethoxycarbonyl groups.

Of the compounds of formula (Ia), a particularly preferred class of compounds for use in the present invention are those compounds in which R¹ represents a formyl group, an alkanoyl group having from 2 to 7 carbon atoms, a halogen-substituted alkanoyl group having from 2 to 4 carbon atoms, an alkoxycarbonyl group having from 2 to 6 carbon atoms, a haloalkoxycarbonyl group having from 3 to 5 carbon atoms or an alkoxyalkoxycarbonyl group having a total of from 4 to 6 carbon atoms. The most preferred compounds are those in which R¹ represents a C₂–C₄ alkanoyl group or a C₂–C₄ alkoxycarbonyl group.

Where the group R² in formula (Ib) represents an alkyl group, this may be a straight or branched chain alkyl group and preferably has from 1 to 4 carbon atoms; examples of such groups include the methyl, ethyl, propyl, isopropyl, butyl and isobutyl groups. Where R² represents a phenyl group, this may be substituted by one or more halogen and/or lower alkyl (preferably methyl) groups; examples of such groups include the phenyl, o-chlorophenyl, p-chlorophenyl, 2,4-dichlorophenyl, o-methylphenyl, m-methylphenyl and p-methylphenyl groups. Where R² represents a benzyl group, it may have one or more halogen and/or alkyl (preferably methyl) substituents in its benzene ring; examples of such groups include the benzyl, o-chlorobenzyl, p-chlorobenzyl, 2,4-dichlorobenzyl and p-methylbenzyl groups.

More preferred classes of compound are those of formula (Ib) in which X represents an iodine atom and:

n is 1 and R represents a straight chain alkyl group having from 1 to 3 carbon atoms or a phenyl group; or n is 2 and R represents a methyl group.

Specific examples of compounds of the present invention are listed below. The compounds are hereafter referred to by the numbers assigned to them in this list.

1. 3-Acetoxy-1,1,2-triiodo-1-propene.
2. 3-Propionyloxy-1,1,2-triiodo-1-propene.
3. 3-Butyryloxy-1,1,2-triiodo-1-propene.
4. 3-Isobutyryloxy-1,1,2-triiodo-1-propene.
5. 3-Valeryloxy-1,1,2-triiodo-1-propene.
6. 3-Isovaleryloxy-1,1,2-triiodo-1-propene.
7. 3-Hexanoyloxy-1,1,2-triiodo-1-propene.
8. 3-Heptanoyloxy-1,1,2-triiodo-1-propene.
9. 3-Octanoyloxy-1,1,2-triiodo-1-propene.
10. 3-Nonanoyloxy-1,1,2-triiodo-1-propene.
11. 3-Decanoyloxy-1,1,2-triiodo-1-propene.
12. 3-Bromoacetoxy-1,1,2-triiodo-1-propene.
13. 3-Chloroacetoxy-1,1,2-triiodo-1-propene.
14. 3-Dichloroacetoxy-1,1,2-triiodo-1-propene.
15. 3-Trichloroacetoxy-1,1,2-triiodo-1-propene.
16. 3-(2-Bromopropionyloxy)-1,1,2-triiodo-1-propene.
17. 3-(3-Bromopropionyloxy)-1,1,2-triiodo-1-propene.
18. 3-(2-Chloropropionyloxy)-1,1,2-triiodo-1-propene.
19. 3-(3-Chloropropionyloxy)-1,1,2-triiodo-1-propene.
20. 3-(2-Bromobutyryloxy)-1,1,2-triiodo-1-propene.
21. 3-(4-Chlorobutyryloxy)-1,1,2-triiodo-1-propene.
22. 3-(2-Bromoisobutyryloxy)-1,1,2-triiodo-1-propene.
23. 3-(2-Bromovaleryloxy)-1,1,2-triiodo-1-propene.
24. 3-(2-Bromohexanoyloxy)-1,1,2-triiodo-1-propene.
25. 3-(6-Bromohexanoyloxy)-1,1,2-triodo-1-propene.
26. 3-(2-Bromooctanoyloxy)-1,1,2-triiodo-1-propene.
27. 3-Methoxycarbonyloxy-1,1,2-triiodo-1-propene.
28. 3-Ethoxycarbonyloxy-1,1,2-triiodo-1-propene.
29. 3-Propoxycarbonyloxy-1,1,2-triiodo-1-propene.

30. 3-Isopropoxycarbonyloxy-1,1,2-triiodo-1-propene.
31. 3-Butoxycarbonyloxy-1,1,2-triiodo-1-propene.
32. 3-Isobutoxycarbonyloxy-1,1,2-triiodo-1-propene.
33. 3-Pentyloxycarbonyloxy-1,1,2-triiodo-1-propene.
34. 3-Isopentyloxycarbonyl-1,1,2-triiodo-1-propene.
35. 3-Hexyloxycarbonyloxy-1,1,2-triiodo-1-propene.
36. 3-Heptyloxycarbonyloxy-1,1,2-triiodo-1-propene.
37. 3-Octyloxycarbonyloxy-1,1,2-triiodo-1-propene.
38. 3-Acetoxy-1-bromo-1,2-diiodo-1-propene.
39. 3-Propionyloxy-1-bromo-1,2-diiodo-1-propene.
40. 3-Butyryloxy-1-bromo-1,2-diiodo-1-propene.
41. 3-Isobutyryloxy-1-bromo-1,2-diiodo-1-propene.
42. 3-Valeryloxy-1-bromo-1,2-diiodo-1-propene.
43. 3-Isovaleryloxy-1-bromo-1,2-diiodo-1-propene.
44. 3-Hexanoyloxy-1-bromo-1,2-diiodo-1-propene.
45. 3-Heptanoyloxy-1-bromo-1,2-diiodo-1-propene.
46. 3-Octanoyloxy-1-bromo-1,2-diiodo-1-propene.
47. 3-Decanoyloxy-1-bromo-1,2-diiodo-1-propene.
48. 3-Bromoacetoxy-1-bromo-1,2-diiodo-1-propene.
49. 3-Chloroacetoxy-1-bromo-1,2-diiodo-1-propene.
50. 3-Dichloroacetoxy-1-bromo-1,2-diiodo-1-propene.
51. 3-Trichloroacetoxy-1-bromo-1,2-diiodo-1-propene.
52. 3-(2-Bromopropionyloxy)-1-bromo-1,2-diiodo-1-propene.
53. 3-(3-Chloropropionyloxy)-1-bromo-1,2-diiodo-1-propene.
54. 3-(2-Bromobutyryloxy)-1-bromo-1,2-diiodo-1-propene.
55. 3-(4-Chlorobutyryloxy)-1-bromo-1,2-diiodo-1-propene.
56. 3-(2-Bromoisobutyryloxy)-1-bromo-1,2-diiodo-1-propene.
57. 3-(2-Bromooctanoyloxy)-1-bromo-1,2-diiodo-1-propene.
58. 3-Methoxycarbonyloxy-1-bromo-1,2-diiodo-1-propene.
59. 3-Ethoxycarbonyloxy-1-bromo-1,2-diiodo-1-propene.
60. 3-Propoxycarbonyloxy-1-bromo-1,2-diiodo-1-propene.
61. 3-Isopropoxycarbonyloxy-1-bromo-1,2-diiodo-1-propene.
62. 3-Butoxycarbonyloxy-1-bromo-1,2-diiodo-1-propene.
63. 3-Isobutoxycarbonyloxy-1-bromo-1,2-diiodo-1-propene.
64. 3-Pentyloxycarbonyloxy-1-bromo-1,2-diiodo-1-propene.
65. 3-Hexyloxycarbonyloxy-1-bromo-1,2-diiodo-1-propene.
66. 3-Octyloxycarbonyloxy-1-bromo-1,2-diiodo-1-propene.
67. 3-(2-Chloroethoxycarbonyloxy)-1,1,2-triiodo-1-propene.
68. 3-(2-Bromoethoxycarbonyloxy)-1,1,2-triiodo-1-propene.
69. 3-(3-Chloropropoxycarbonyloxy)-1,1,2-triiodo-1-propene.
70. 3-(4-Chlorobutoxycarbonyloxy)-1,1,2-triiodo-1-propene.
71. 3-(6-Chlorohexyloxycarbonyloxy)-1,1,2-triiodo-1-propene.
72. 3-(2-Methoxyethoxycarbonyloxy)-1,1,2-triiodo-1-propene.
73. 3-(2-Ethoxyethoxycarbonyloxy)-1,1,2-triiodo-1-propene.
74. 3-(2-Butoxyethoxycarbonyloxy)-1,1,2-triiodo-1-propene.
75. 3-[2-(2-Chloroethoxy)ethoxycarbonyloxy]-1,1,2-triiodo-1-propene.
76. 3-(2-Chloroethoxycarbonyloxy)-1-bromo-1,2-diiodo-1-propene.
77. 3-(2-Bromoethoxycarbonyloxy)-1-bromo-1,2-diiodo-1-propene.
78. 3-(4-Chlorobutoxycarbonyloxy)-1-bromo-1,2-diiodo-1-propene.
79. 3-(2-Ethoxyethoxycarbonyloxy)-1-bromo-1,2-diiodo-1-propene.
80. 3-(2-Butoxyethoxycarbonyloxy)-1-bromo-1,2-diiodo-1-propene.
81. 3-Formyloxy-1,1,2-triiodo-1-propene.
82. 3-Formyloxy-1-bromo-1,2-diiodo-1-propene.
83. 3-Methoxycarbonylmethoxy-1,1,2-triiodo-1-propene.
84. 3-Ethoxycarbonylmethoxy-1,1,2-triiodo-1-propene.
85. 3-Propoxycarbonylmethoxy-1,1,2-triiodo-1-propene.
86. 3-Isopropoxycarbonylmethoxy-1,1,2-triiodo-1-propene.
87. 3-Butoxycarbonylmethoxy-1,1,2-triiodo-1-propene.
88. 3-Methoxycarbonylmethoxy-1-bromo-1,2-diiodo-1-propene.
89. 3-Ethoxycarbonylmethoxy-1-bromo-1,2-diiodo-1-propene.
90. 3-Propoxycarbonylmethoxy-1-bromo-1,2-diiodo-1-propene.
91. 3-Benzyloxycarbonylmethoxy-1,1,2-triiodo-1-propene.
92. 3-p-Chlorobenzyloxycarbonylmethoxy-1,1,2-triiodo-1-propene.
93. 3-Phenoxycarbonylmethoxy-1,1,2-triiodo-1-propene.
94. 3-Phenoxycarbonylmethoxy-1-bromo-1,2-diiodo-1-propene.
95. 3-p-Chlorophenoxycarbonylmethoxy-1,1,2-triiodo-1-propene.
96. 3-o-Methylphenoxycarbonylmethoxy-1,1,2-triiodo-1-propene.
97. 3-m-Methylphenoxycarbonylmethoxy-1,1,2-triiodo-1-propene.
98. 3-p-Methylphenoxycarbonylmethoxy-1,1,2-triiodo-1-propene.
99. 3-(2,4-Dichlorophenoxycarbonylmethoxy)-1,1,2-triiodo-1-propene.
100. 3-(2-Methoxycarbonylethoxy)-1,1,2-triiodo-1-propene.
101. 3-(2-Ethoxycarbonylethoxy)-1,1,2-triiodo-1-propene.
102. 3-(2-Propoxycarbonylethoxy)-1,1,2-triiodo-1-propene.
103. 3-(2-Butoxycarbonylethoxy)-1,1,2-triiodo-1-propene.
104. 3-(2-Phenoxycarbonylethoxy)-1,1,2-triiodo-1-propene.
105. 3-(2-p-Chlorobenzyloxycarbonylethoxy)-1,1,2-triiodo-1-propene.

Of the compounds listed above, particularly preferred compounds are Compounds No. 1, 28, 38, 59, 83 and 100.

The compounds of the invention may be prepared by methods well-known for the preparation of analogous compounds, for example as illustrated by the following Methods.

METHOD A

Compounds of formula (Ia) may be prepared as illustrated by the following reaction scheme:

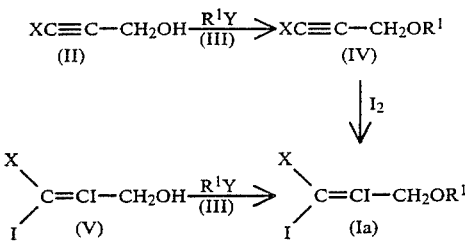

in which X and $R^1$ are as defined above and Y represents a halogen atom, preferably a chlorine atom. More specifically, a 3-halopropargyl alcohol of formula (II) is reacted with an acid halide or halocarbonate of formula (III) and the resulting product is contacted with iodine to give the desired product of formula (Ia). Alternatively, a 2,3,3-trihaloallyl alcohol of formula (V) may be reacted with an acid halide or halocarbonate of formula (III) to give the desired compound of formula (Ia) directly.

The compound of formula (II) in which X represents a bromine atom may be obtained by reacting propargyl alcohol with bromine and the compound of formula (IIa) may be prepared by reacting the corresponding compound of formula (II) with iodine.

METHOD B

Compounds of formula (Ia) in which $R^1$ represents a formyl group may be obtained by reacting a 2,3,3-trihaloallyl alcohol of formula (V) with formic acid of formula (VI) or with a reactive derivative thereof, as illustrated by the following reaction scheme:

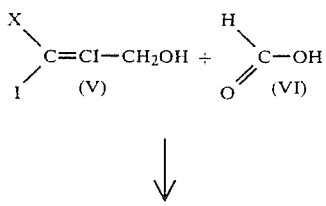

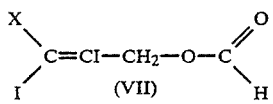

in which X is as defined above.

METHOD C

Compounds of formula (Ib) may be obtained by the reaction summarized in the following scheme:

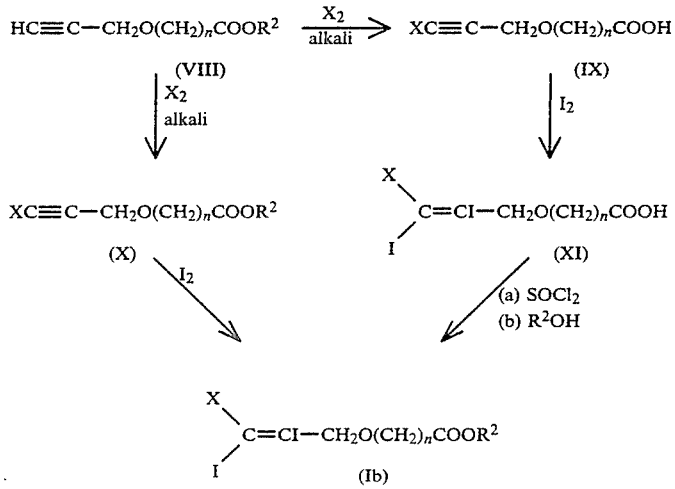

In the above formulae, X, n and $R^2$ are as defined above.

In one of the two routes illustrated by the above reaction scheme, the propargyl derivative of formula (VIII) is reacted with iodine or bromine in the presence of more than two molar equivalents of alkali. The amount of iodine or bromine is preferably about one molar equivalent. By using this amount of alkali there is obtained a monohalogenated acid compound of formula (IX), which is reacted with one molar equivalent of iodine to give a compound of formula (XI). This compound of formula (XI) is converted to its corresponding acid chloride by reaction with thionyl chloride under conventional conditions and the resulting product is contacted with an alcohol to give the desired ester of formula (Ib).

Alternatively, if the propargyl derivative of formula (VIII) is reacted with iodine or bromine (preferably about one molar equivalent) in the presence of one molar equivalent of alkali, a halogenated ester of formula (X) is obtained and this may then be converted to the desired compound of formula (Ib) by reaction with iodine.

The propargyl derivative of formula (VIII) in which n is 1 can be obtained by reacting propargyl alcohol with a haloacetic acid ester in the presence of an alkali and the propargyl derivative of formula (VIII) in which n is 2 can be obtained by reacting propargyl alcohol with an acrylic acid ester in the presence of an alkali.

The compounds of the invention have been found to be useful as anti-fungal and preservative agents. They are effective against a wide range of fungi, particularly those of the genera Penicillium, Aspergillus, Rhizopus, Chaetomium, Cladosporium, Fusarium, Pullularia and Aureobasidium, as well as a wide variety of other fungi, including those belonging to the genus Trichoderma and wood-staining fungi. However, the use of the compounds of the invention is not restricted to these particular genera of fungi. The compounds of the invention are also useful to preserve materials from damage by wood-rotting and soft-rotting fungi.

Materials which may be preserved and protected from the harmful effects of fungal attack by means of the compounds of the invention include, particularly, wood, as well as a variety of industrial materials, such as wet pulp, paper, mats, fibres, leather, adhesives, paints and synthetic resins; however, in general, any organic materials susceptible to deterioration by fungal attack may be protected by the compounds of the invention.

Where the compounds of the invention are employed in the form of a composition in admixture with a carrier, diluent or adjuvant, the proportion of the compound may vary over a wide range, depending upon the nature of the composition, the material to be treated and the method of application of the composition. In general, the compound of the invention preferably forms from 0.005 to 95% by weight of the composition, more preferably from 0.1 to 50% by weight, and most preferably from 0.2 to 15% by weight, although the preferred concentration will vary depending upon the nature of the composition itself.

Examples of formulations to be adopted by the composition of the invention include: oil-soluble preparations, emulsions, pastes, powders, wettable powders, aerosols and paints, as well as many other forms well-known to those skilled in the art.

Suitable carriers include: inert solid carriers, such as clay, talc, bentonite, kaolin, silicic anhydride, calcium carbonate and wood meal; liquid carriers, such as kerosene, ligroin, the xylenes, methylnaphthalene, dimethylformamide and dimethyl sulphoxide; and vapour carriers, such as nitrogen gas, dimethyl ether, the vapourizable fluorocarbons and chlorofluorocarbons (such as those sold under the Trade Mark "Freon") and monomeric vinyl chloride. In order to improve the properties of the composition and/or to enhance its anti-fungal and preservative effects, any suitable auxiliary agent may be employed in addition to these carriers. Examples include anionic, cationic and non-ionic surface active agents and various high molecular weight compounds, e.g. methylcellulose, vinyl acetate resins and sodium alginate.

It is, of course, also possible to enhance the anti-fungal or preservative effect of the composition by using the compounds of the invention in admixture with other anti-fungal or preservative agents, such as 2-(4-thiazolyl)benzimidazole (Thiabendazole), N,N-dimethyl-N'-dichlorofluoromethylthio-N'-phenylsulphamide (Dichlofluanid), iodopropargyl compounds (e.g. 4-chlorophenyl-3'-iodopropargylformal), halogenated phenols (e.g. tribromophenol or trichlorophenol), trialkyltin or triaryltin compounds (e.g. bis-tributyltin oxide, tributyltin phthalate or triphenyltin hydroxide), N-nitroso-N-cyclohexylhydroxylamine metal salts (e.g. the aluminium salt) or benzanilides (e.g. 4'-chlorobenzanilide). Insecticides may also be employed in association with the compounds of the invention, for example chlordane, permethrin or phoxim.

The anti-fungal and preservative activities of the compounds of the invention are illustrated by the following Experiments.

EXPERIMENT 1

Light stability

Each of the compounds under test was dissolved in ethylene glycol monomethyl ether to form a 0.5% w/v solution. Each solution was then exposed to ultraviolet radiation for 2 hours using a sterilization lamp. Into each of the irradiated solutions was immersed a paper disk of diameter 8 mm; after removal of excess solution, each disc was then air-dried.

Using the paper discs thus prepared, the anti-fungal and preservative activities of the compounds under test were tested by the paper diffusion method. Anti-fungal activity was examined using an agar medium containing a mixture of spores of *Aspergillus niger, Trichoderma viride, Fusarium moniliforme* and *Pullularia pullulans*. Preservative activity was examined using an agar medium containing either the fungus *Tyromyces palustris* or the fungus *Pycnoporus coccineus*. The temperature was maintained at 25° C. and the anti-fungal activity was determined after cultivation for 5 days; the preservative activity was determined after cultivation for 9 days.

These experiments were carried out using various of the compounds of the invention as well as the known compounds, triiodoallyl alcohol and its methyl ether, as controls. The results are shown in Tables 1 and 2, in which the compounds of the invention are identified by the numbers assigned to them in the foregoing list.

The following ratings are used to indicate anti-fungal and preservative activities:

+: Zone of inhibition of fungal growth is observed around the paper disc;

±: no zone of inhibition of fungal growth is observed around the paper disc, but growth of fungi on the paper disc is inhibited;

−: growth of fungi is observed on the paper disc.

TABLE 1

| Compound No. | Anti-fungal activity | Compound No. | Anti-fungal activity |
| --- | --- | --- | --- |
| 2 | + | 55 | ± |
| 3 | + | 58 | + |
| 5 | + | 59 | + |
| 12 | + | 60 | + |
| 13 | + | 67 | + |
| 16 | ± | 73 | + |
| 21 | ± | 75 | + |
| 27 | + | 77 | + |
| 28 | + | triiodo-allyl alcohol | − |
| 29 | + | | |
| 31 | ± | triiodo-allyl methyl ether | − |
| 32 | ± | | |
| 49 | ± | | |

TABLE 2

| | Preservative activity | | | Preservative Activity | |
| --- | --- | --- | --- | --- | --- |
| Compound No. | Tyromyces palustris | Pycnoporus coccineus | Compound No. | Tyromyces palustris | Pycnoporus coccineus |
| 1 | ± | + | 36 | + | + |
| 2 | + | + | 37 | ± | ± |
| 3 | + | + | 40 | + | + |
| 5 | + | + | 42 | + | + |
| 7 | + | + | 49 | ± | + |
| 8 | ± | ± | 55 | + | + |
| 13 | ± | + | 58 | + | ± |

TABLE 2-continued

| Compound No. | Preservative activity Tyromyces palustris | Pycnoporus coccineus | Compound No. | Preservative Activity Tyromyces palustris | Pycnoporus coccineus |
|---|---|---|---|---|---|
| 16 | + | + | 59 | + | + |
| 21 | + | + | 60 | + | + |
| 27 | + | ± | 61 | + | + |
| 28 | + | + | 62 | + | + |
| 29 | + | + | 64 | + | + |
| 31 | + | + | 70 | + | + |
| 33 | + | + | 73 | + | + |
| 35 | + | + | 77 | + | + |
| triiodoallyl alcohol | − | − | triiodoallyl methyl ether | − | − |

Identical tests were carried out using the compounds of the invention and the two controls, except that the ultraviolet irradiation was omitted; in all cases, both the compounds of the invention and the controls had a rating of +.

EXPERIMENT 2

Anti-fungal activity

Each of the compounds under test was dissolved in dimethylformamide to produce a 1% w/v solution. Pieces of moso bamboo and beech were then cut to 2×2×0.2 cm to produce test samples. These test samples were then each dipped in one of the test solutions for 5 seconds, air-dried, washed with water (at a supply rate of about 2 liters/minute) for 1 hour, air-dried for 24 hours, heated at 60° C. for 24 hours and finally sterilized by dry air.

Each test sample was then tested for its resistance to fungal growth by a method based on the procedure prescribed by Japanese Industrial Standard (JIS) Z 2911. Specifically, a suspension of one of the test fungi described below was innoculated into each test sample and then cultivated at 25° C. for 3 weeks in a sterile petri dish containing a wet filter paper.

The fungi used were as follows:
*Aspergillus niger* Test fungus No. 1
*Trichoderma viride* Test fungus No. 2
*Fusarium moniliforme* Test fungus No. 3
*Pullularia pullulans* Test fungus No. 4.

The growth of the mycelium was examined and the results are shown in Table 3, using the following ratings:

+: No growth of fungus was observed on test sample;
±: only slight growth of fungus was observed on test sample;
−: growth of fungus was observed on test sample.

The compounds of the invention are identified by the numbers assigned to them in the foregoing list and, as a control, the known anti-fungal agent, pentachlorophenol (PCP) laurate was also used. Untreated control samples of the two woods were also exposed to the various fungi.

TABLE 3

| Compound No. | Anti-fungal activity Moso bamboo test fungus No. | | | | Beech test fungus No. | | | |
|---|---|---|---|---|---|---|---|---|
| | 1 | 2 | 3 | 4 | 1 | 2 | 3 | 4 |
| 1 | + | + | + | + | + | + | + | + |
| 2 | + | + | + | + | + | + | + | + |

TABLE 3-continued

| Compound No. | Anti-fungal activity Moso bamboo test fungus No. | | | | Beech test fungus No. | | | |
|---|---|---|---|---|---|---|---|---|
| | 1 | 2 | 3 | 4 | 1 | 2 | 3 | 4 |
| 3 | + | + | + | + | + | + | + | + |
| 4 | + | + | + | + | + | + | + | + |
| 5 | + | ± | + | + | + | + | + | + |
| 7 | + | + | − | + | + | + | ± | + |
| 8 | + | ± | ± | + | + | ± | + | + |
| 9 | + | ± | + | ± | + | ± | + | + |
| 10 | + | ± | ± | ± | + | ± | + | + |
| 12 | + | + | + | + | + | + | + | + |
| 13 | + | − | + | + | + | ± | + | + |
| 14 | + | + | + | + | + | + | + | + |
| 15 | + | + | + | + | + | + | + | + |
| 16 | + | + | + | + | + | + | + | + |
| 21 | + | + | + | + | + | + | + | + |
| 27 | + | + | + | + | + | + | + | + |
| 28 | + | + | + | + | + | + | + | + |
| 29 | + | + | + | + | + | + | + | + |
| 30 | + | ± | ± | + | + | + | + | + |
| 31 | + | + | ± | ± | + | + | + | + |
| 32 | + | + | ± | ± | + | + | + | + |
| 33 | + | ± | − | ± | + | ± | − | + |
| 35 | + | ± | − | ± | + | + | − | + |
| 36 | + | ± | − | ± | + | ± | ± | + |
| 37 | + | ± | ± | ± | + | ± | + | + |
| 38 | + | + | + | + | + | + | + | + |
| 39 | + | + | + | + | + | + | + | + |
| 40 | + | − | + | + | + | − | + | + |
| 42 | + | ± | + | + | + | + | + | + |
| 48 | + | + | + | + | + | + | + | + |
| 49 | + | + | + | + | + | + | + | + |
| 50 | + | + | + | + | + | + | + | + |
| 51 | + | + | + | + | + | + | + | + |
| 52 | + | ± | + | + | + | ± | + | + |
| 55 | + | + | + | + | + | + | + | + |
| 56 | + | + | + | + | + | + | + | + |
| 58 | + | + | + | + | + | + | + | + |
| 59 | + | + | + | + | + | + | + | + |
| 60 | + | + | + | + | + | + | + | + |
| 62 | + | + | + | + | + | + | + | + |
| 64 | + | + | + | + | + | + | + | + |
| 65 | + | + | ± | ± | + | + | + | + |
| 67 | + | ± | ± | + | + | ± | + | + |
| 70 | + | − | ± | + | + | − | + | + |
| 75 | + | + | + | + | + | + | + | + |
| 77 | + | + | ± | + | + | + | + | + |
| 81 | + | + | + | + | + | + | + | + |
| 82 | + | + | + | + | + | + | + | + |
| 83 | + | + | + | + | + | + | + | + |
| 84 | + | + | + | + | + | + | + | + |
| 85 | + | + | + | + | + | + | + | + |
| 87 | + | + | ± | ± | + | + | ± | + |
| 88 | + | − | + | + | + | − | + | + |
| 89 | + | ± | ± | ± | + | ± | + | + |
| 91 | + | − | + | + | + | ± | + | + |
| 93 | + | + | ± | ± | + | + | ± | + |
| 96 | + | − | + | ± | + | ± | + | + |
| 100 | + | + | + | + | + | + | + | + |
| 101 | + | + | ± | + | + | + | + | + |
| PCP laurate | − | + | − | − | ± | + | − | − |
| Untreated control | − | − | − | − | − | − | − | − |

EXPERIMENT 3

Wood preservative activity

This test is based upon the procedure of JIS A-9302.

Each test compound was dissolved in methanol to produce a 0.05% w/v solution. The compounds under test were the compounds of the invention, identified by the numbers assigned to them in the foregoing list, and pentachlorophenol (PCP).

Meanwhile, pieces of sugi sapwood were cut into test samples of dimensions 2×2×1 cm and each sample was impregnated under reduced pressure with one of the test solutions and then air-dried. After this treatment, the test samples were weathered by subjecting them twice to the following sequence of operations: leaching with water (at a supply rate of about 2 liters/minute) for 5 hours; air-drying for 24 hours; and heating at 60° C. for 24 hours. After this, the samples were sterilized by dry air.

The test samples thus prepared were each placed upon fungal mycelia of the lignin-decomposing fungus, *Coriolus versicolor* or the cellulose-decomposing fungus, *Tyromyces palustris*, which had been previously incubated in a sterile petri dish containing a medium including 2% malt extract, 1% glucose and 0.5% peptone. The samples were then subjected to force decay by the fungi at 25° C. for 3 weeks. The growth of the mycelia on the samples and the reduction in compressive strength of the samples were determined in order to estimate the preservative activities of the compounds under test. The results are shown in Table 4, in which the preservative activity is indicated by the following ratings:

+: No fungal growth is observed on the test samples and there is no change in compressive strength;

±: a slight growth of mycelium is observed on the test samples or the compressive strength is reduced slightly;

−: growth of mycelium is observed on the test sample or its compressive strength is reduced significantly.

TABLE 4

| Compound No. | Preservative activity Coriolus versicolor | Tyromyces palustris | Compound No. | Preservative activity Coriolus versicolor | Tyromyces palustris |
| --- | --- | --- | --- | --- | --- |
| 1 | + | + | 59 | + | ± |
| 2 | + | + | 60 | + | ± |
| 3 | + | + | 62 | + | + |
| 4 | ± | ± | 64 | + | ± |
| 5 | + | + | 67 | ± | ± |
| 7 | + | + | 70 | ± | ± |
| 8 | + | + | 73 | + | + |
| 9 | ± | ± | 77 | + | ± |
| 10 | + | ± | 81 | + | + |
| 11 | + | ± | 82 | + | + |
| 12 | + | ± | 83 | + | + |
| 13 | ± | ± | 84 | + | + |
| 14 | + | ± | 85 | + | + |
| 15 | + | ± | 87 | ± | + |
| 16 | + | + | 88 | + | ± |
| 21 | + | + | 89 | + | ± |
| 27 | + | + | 90 | + | ± |
| 28 | + | + | 91 | ± | + |
| 29 | + | + | 92 | ± | + |
| 30 | ± | + | 93 | + | + |
| 31 | + | + | 95 | ± | ± |
| 32 | + | + | 96 | + | ± |
| 33 | + | + | 97 | ± | ± |
| 35 | + | + | 98 | ± | ± |
| 36 | + | + | 99 | ± | ± |
| 37 | + | + | 100 | + | + |
| 38 | + | ± | 101 | ± | + |
| 40 | + | ± | 102 | + | + |
| 42 | + | + | 103 | ± | + |
| 49 | + | ± | 104 | ± | ± |
| 50 | + | ± | 105 | ± | ± |
| 55 | + | ± | PCP | − | ± |
| 56 | ± | ± | Untreated control | − | − |
| 58 | + | ± | | | |

EXPERIMENT 4

Resistance to ultraviolet radiation

Each test compound was dissolved in 5 ml of ethylene glycol monomethyl ether to produce a solution of concentration 0.2% w/v. The solutions were each placed in a weighing bottle and irradiated with ultraviolet radiation from a 15 watt sterilization lamp at a distance of 18 cm for 10 hours for the compounds of the invention and for 1 hour for the Comparative Compound.

A paper disc of diameter 8 mm was dipped into one of the irradiated solutions, excess solution was removed with a paper and then the paper disc were dried. After this, the anti-fungal activity of each compound was examined by the diffusion method using a petri dish of diameter 45 mm and 4 ml of an agar medium containing a mixture of fungi. The mixtures of test fungi used in this Experiment were identified by the following codes:

(i): a mixture of wood-decaying fungi, i.e. *Coriolus versicolor*, *Tyromyces palustris* and *Pycnoporus coccineus*;

(ii): mixtures of other fungi, i.e. *Trichoderma viride*, *Fusarium moniliforme*, *Aspergillus niger* and *Pullularia pullulans*.

Mixture (i) was incubated for 7 days; mixture (ii) was incubated for 12 days.

The ability of the compounds under test to resist fungal attack was assessed and the results are reported in Table 5, in which the following ratings were used:

+: zone of inhibition of fungal growth was observed around the paper disc;

−: growth of fungi was observed on the paper disc.

TABLE 5

| Compound No. | Fungus (i) | (ii) |
| --- | --- | --- |
| 1 | + | + |
| 28 | + | + |
| 38 | + | + |
| 59 | + | + |
| triiodoallyl alcohol | − | − |

EXPERIMENT 5

Resistance to ultraviolet radiation

The tests described in Experiment 4 were repeated, except that the concentration of the solution was 0.3% w/v, the period of irradiation was 20 hours for both the compounds of the invention and the Comparative Compounds, the petri dishes used had a diameter of 35 mm and contained 3 ml of agar medium, and the incubation period was 7 days. The results are reported in Table 6.

TABLE 6

| Compound No. | Fungus mixture (i) | (ii) |
| --- | --- | --- |
| 1 | + | + |
| 28 | + | + |
| 38 | + | + |
| 59 | + | + |
| triiodoallyl methyl ether | − | − |

The invention is further illustrated by the following Examples, of which Examples 1 to 9 illustrate the preparation of compounds of the invention and Examples 10 to 23 illustrate the preparation of anti-fungal and preservative compositions of the invention.

EXAMPLE 1

3-Ethoxycarbonyloxy-1,1,2-triiodo-1-propene
(Compound No. 28)

6 g of iodopropargyl alcohol were dissolved in 30 ml of water and the solution was cooled to 5° C. 3.7 g of ethyl chlorocarbonate and a solution of 2.2 g of 85% w/w potassium hydroxide in 10 ml of water were gradually added dropwise and simultaneously. After the addition was complete, the resulting mixture was stirred for 2 hours and then 8.45 g of iodine were added little by little to the solution. The resulting mixture was stirred for a further 3 hours at room temperature, after which it was extracted with ethyl acetate. The extract was washed with water and dried over anhydrous sodium sulphate. The solvent was then distilled off under reduced pressure and the resulting crystals were recrystallized from a mixture of ethyl acetate and hexane to give 6.9 g of the desired Compound No. 28, melting at 49°–50° C.

Elemental Analysis:

Calculated for $C_6H_7O_3I_3$: C, 14.19%; H, 1.38%; I, 74.97%. Found: C, 14.05%; H, 1.26%; I, 75.22%.

Infrared Absorption spectrum (Nujol-trade mark) $\nu_{max}$cm$^{-1}$ 1740.

EXAMPLE 2

3-Octanoyloxy-1,1,2-triiodo-1-propane (Compound No. 9)

2.0 g of 1,1,2-triiodoallyl alcohol were dissolved in 10 ml of pyridine; 0.9 g of octanoyl chloride were then added dropwise to the solution, with stirring and ice-cooling. The resulting mixture was left to stand overnight at room temperature, after which the reaction mixture was poured into ice and water and extracted with ethyl acetate. The extract was washed with water and dried over anhydrous sodium sulphate. The solvent was distilled off under reduced pressure and the oily substance thus obtained was adsorbed in a dry silica gel chromatography column and eluted with a 3:1 by volume mixture of hexane and ethyl acetate to give 2.4 g of the desired Compound No. 9 as an oil.

Elemental Analysis:

Calculated for $C_{11}H_{17}O_2I_3$: C, 23.51%; H, 3.05%; I, 67.74%. Found: C, 23.81%; H, 3.22%; I, 67.80%.

Infrared absorption spectrum (liquid film) $\nu_{max}$ cm$^{-1}$: 1740.

Rf value (thin layer chromatography on silica gel developed with a 1:1 by volume mixture of hexane and ethyl acetate): 0.59.

EXAMPLE 3

3-(4-Chlorobutyryloxy)-1-bromo-1,2-diiodo-1-propane
(Compound No. 55)

5.6 g of propargyl alcohol were dissolved in 100 ml of water; to this solution were gradually added dropwise and simultaneously a solution of 16 g of bromine in 20 ml of water and a solution of 7.2 g of 85% w/w potassium hydroxide in 20 ml of water. When the addition was complete, the solution was stirred for 3 hours, after which 25.4 g of iodine and a solution of 7.2 g of 85% w/w potassium hydroxide in 20 ml of water were added. After stirring the mixture for a further 3 hours at room temperature, it was extracted with ethyl acetate and the extract was washed with water and dried over anhydrous sodium sulphate. The solvent was then distilled off under reduced pressure and the crystals thus obtained were recrystallized from a mixture of ethyl acetate and hexane to give 22 g of 3-bromo-2,3-diiodoallyl alcohol, melting at 149°–151° C.

Elemental Analysis:

Calculated for $C_3H_3OBrI_2$: C, 9.26%; H, 0.78%; Br, 20.56%; I, 65.28%. Found: C, 9.32%; H, 0.83%; Br, 20.62%; I, 65.59%.

1.0 g of 3-bromo-2,3-diiodoallyl alcohol prepared as described above was dissolved in 7 ml of pyridine. To this solution was added dropwise 0.4 g of 4-chlorobutyryl chloride, with ice-cooling and stirring. The reaction mixture was then allowed to stand overnight at room temperature, after which it was diluted with water and extracted with ethyl acetate. The extract was washed with water and dried over anhydrous sodium sulphate, after which the solvent was distilled off under reduced pressure. The resulting oily substance was adsorbed in a dry silica gel chromatography column and eluted with a 3:1 by volume mixture of hexane and ethyl acetate to give 0.9 g of the desired Compound No. 55 as an oil.

Elemental Analysis:

Calculated for $C_7H_8O_2ClBrI_2$: C, 17.04%; H, 1.63%; Cl, 7.19%; Br, 16.20%; I, 51.45% Found: C, 16.88%; H, 1.56%; Cl, 6.93%; Br, 15.96%; I, 51.70%.

Infrared absorption spectrum (liquid film) $\nu_{max}$ cm$^{-1}$: 1740

Rf value (thin layer chromatography on silica gel developed with a 1:1 by volume mixture of hexane and ethyl acetate): 0.45.

Following the procedures described in Examples 1 to 3, the compounds mentioned in Table 7 were prepared. The compounds are identified by the number assigned to them in the foregoing list. Where the compound was prepared in the form of crystals, the melting point is given; where it was prepared in the form of an oil, this is stated and the Rf value is given. The Rf value was obtained from thin layer chromatography on silica gel developed with a 1:1 by volume mixture of hexane and benzene.

Also given are the corresponding properties of the compounds prepared in Examples 1–3.

TABLE 7

| Compound No. | Melting Point (°C.) or Rf value | Infrared Absorption Spectrum (cm$^{-1}$) |
|---|---|---|
| 1 | 43–44 | 1740 |
| 2 | oil 0.42 | 1740 |
| 3 | oil 0.47 | 1735 |
| 4 | 56–57 | 1740 |
| 5 | oil 0.51 | 1735 |
| 7 | oil 0.55 | 1738 |
| 8 | oil 0.57 | 1740 |
| 9 | oil 0.59 | 1740 |
| 10 | oil 0.61 | 1740 |
| 11 | oil 0.63 | 1740 |
| 12 | 88–90 | 1760 |
| 13 | 85–87 | 1770 |
| 14 | oil 0.62 | 1770 |
| 15 | oil 0.78 | 1765 |
| 16 | oil 0.54 | 1740 |
| 21 | oil 0.40 | 1740 |
| 22 | oil 0.61 | 1735 |
| 27 | 62–63 | 1730 |
| 28 | 49–50 | 1740 |
| 29 | oil 0.45 | 1745 |
| 30 | oil 0.44 | 1740 |
| 31 | oil 0.50 | 1750 |
| 32 | oil 0.51 | 1750 |
| 33 | oil 0.54 | 1750 |
| 35 | oil 0.58 | 1740 |
| 36 | oil 0.60 | 1750 |
| 37 | oil 0.62 | 1750 |
| 39 | oil 0.60 | 1740 |

TABLE 7-continued

| Compound No. | Melting Point (°C.) or Rf value | Infrared Absorption Spectrum (cm$^{-1}$) |
|---|---|---|
| 40 | oil 0.55 | 1730 |
| 42 | oil 0.51 | 1740 |
| 48 | oil 0.46 | 1740 |
| 49 | oil 0.44 | 1760 |
| 50 | oil 0.64 | 1770 |
| 51 | oil 0.84 | 1768 |
| 52 | oil 0.61 | 1740 |
| 55 | oil 0.45 | 1740 |
| 56 | oil 0.68 | 1735 |
| 58 | 58–60 | 1730 |
| 59 | 40–43 | 1730 |
| 60 | oil 0.51 | 1740 |
| 62 | oil 0.60 | 1740 |
| 64 | oil 0.63 | 1740 |
| 65 | oil 0.63 | 1745 |
| 67 | oil 0.38 | 1750 |
| 70 | oil 0.37 | 1745 |
| 73 | oil 0.07 | 1750 |
| 75 | oil 0.12 | 1750 |
| 77 | oil 0.41 | 1750 |

EXAMPLE 4

3-Formyloxy-1,1,2-triiodo-1-propene (Compound No. 81)

2.0 g of 2,3,3-triiodoallyl alcohol and 30 ml of formic acid were refluxed, with stirring, for 3 hours. After cooling the mixture, the crystals which precipitated were collected by filtration, dissolved in ethyl acetate, adsorbed in a dry silica gel chromatography column and eluted with 3:1 by volume mixture of hexane and ethyl acetate, to give 1.8 g of the desired Compound No. 81 in the form of crystals melting at 84°–85° C.

Infrared absorption spectrum (Nujol) $\nu_{max}$ cm$^{-1}$. 1700.

EXAMPLE 5

3-Formyloxy-1-bromo-1,2-diiodo-1-propene (Compound No. 82)

Following the procedure described in Example 4, but using 3-bromo-2,3-diiodoallyl alcohol, the desired Compound No. 82 was obtained in the form of crystals melting at 66°–67° C.

Infrared absorption spectrum (Nujol) $\nu_{max}$ cm$^{-1}$: 1720.

EXAMPLE 6

3-Methoxycarbonylmethoxy-1,1,2-triiodo-1-propane (Compound No. 83)

To an anhydrous solution containing 5.1 g of 55% oily sodium hydride in 120 ml of diethyl ether were added 24 ml of an anhydrous diethyl ether solution containing 5.6 g of propargyl alcohol. The mixture was stirred at room temperature for 1.5 hours, after which 20.9 g of ethyl bromoacetate were added dropwise. The mixture was allowed to stand overnight, after which the excess sodium hydride was decomposed with methanol. After separating off the precipitate produced, the filtrate was distilled to give 10 g of ethyl α-propargyloxyacetate, boiling at 52°–60° C./4–7 mmHg.

Infrared absorption spectrum (liquid film) $\nu_{max}$ cm$^{-1}$: 3300, 2125, 1750.

Rf value (thin layer chromatography on silica gel developed with a 3:1 by volume mixture of hexane and ethyl acetate) 0.43.

To an aqueous solution containing 10 g of the ethyl α-propargyloxyacetate produced as described above and 9.3 g of 85% w/w potassium hydroxide were added 17.8 g of iodine at 0°–5° C. The mixtures was then stirred for 4 hours.

A portion of this reaction mixture was acidified by the addition of hydrochloric acid and extracted with ethyl acetate. The extract was washed with water and dried. The solvent was distilled off and the resulting crude crystals were purified by thin layer chromatography on silica gel developed with a 10:1 by volume mixture of ethyl acetate and hexane, to give 3-iodopropargyloxyacetic acid, melting at 102°–104° C.

To the remainder of the reaction mixture were added a further 17.8 g of iodine and the mixture was then stirred at room temperature for 5 hours. The mixture was acidified with hydrochloric acid and extracted with ethyl acetate. The extract was washed, in turn, with an aqueous solution of sodium hydrosulphite and water, after which it was dried. The solvent was distilled off and the resulting crystals were recrystallized from a mixture of ethyl acetate and hexane to give 28.13 g of 2,2,3-triiodoallyloxyacetic acid, melting at 94°–95° C.

3 g of thionyl chloride were added to 2 g of the triiodoallyloxyacetic acid prepared as described above and the mixture was stirred at room temperature for 1.5 hours. The excess thionyl chloride was then removed. The reaction mixture was then mixed with 10 ml of methanol and 0.5 ml of pyridine and left to stand overnight. The product was purified by column chromatography through silica gel eluted with a 4:1 by volume mixture of ethyl acetate and hexane, to give 0.95 g of the desired Compound No. 83, melting at 67°–68° C.

Elemental Analysis:

Calculated for $C_6H_7I_3O_3$: C, 14.19%; H, 1.39%; I, 74.97%. Found: C, 14.46%; H, 1.41%; I, 74.79%.

Infrared absorption spectrum (Nujol) $\nu_{max}$ cm$^{-1}$: 1735.

EXAMPLE 7

3-Ethoxycarbonylmethoxy-1,1,2-triiodo-1-propane (Compound No. 84)

21.5 g of ethyl α-propargyloxyacetate were dissolved in 300 ml of ethanol, and 20.4 g of sodium ethoxide were added to the solution at 5°–10° C. 37.5 g of iodine were then added to the mixture over 15 minutes, after which it was maintained at that temperature for 30 minutes and then stirred at room temperature for 1 hour. The reaction mixture was then mixed successively with 5 ml of acetic acid and 37.5 g of iodine and then stirred at room temperature for 3 hours, after which it was left to stand overnight. The reaction mixture was then diluted with 200 ml of water and extracted with ethyl acetate. The extract was washed in turn with an aqueous solution of sodium hydrosulphite, an aqueous solution of sodium bicarbonate and water and then dried over anhydrous sodium sulphate. The solvent was then distilled off and the resulting crystals were recrystallized from a mixture of ethyl acetate and hexane, to give 59 g of the desired Compound No. 84, melting at 73°–74° C.

Infrared absorption spectrum (Nujol) $\nu_{max}$ cm$^{-1}$: 1730.

Elemental Analysis:

Calculated for $C_7H_9I_3O_3$: C, 16.11%; H, 1.74%; I, 72.95%. Found: C, 16.07%; H, 1.66%; I, 73.19%.

EXAMPLE 8

3-Ethoxycarbonylmethoxy-1,1,2-triiodo-1-propane (Compound No. 84)

2.84 g of ethyl α-propargyloxyacetate were suspended in water, and 5.1 g of iodine and 2 ml of an aqueous solution containing 1.32 g of 85% w/w potassium hydroxide were simultaneously added dropwise thereto at 0°-3° C. After stirring the mixture at that temperature for 3 hours, it was mixed with 5.1 g of iodine and stirred at room temperature for 2 hours, after which it was left to stand overnight. The reaction mixture was then extracted with ethyl acetate and the extract was washed, in turn, with an aqueous solution of sodium hydrosulphite, an aqueous solution of sodium bicarbonate and water; it was then dried. After distilling off the solvent, the resulting residue was purified by column chromatography on silica gel to give 1.7 g of the desired Compound No. 84, melting at 73°-74° C. The infrared absorption spectrum of this compound agreed with that of the compound obtained in Example 7.

EXAMPLE 9

3-(2-Ethoxycarbonylethoxy)-1,1,2-triiodo-1-propane (Compound No. 101)

25.8 g of methyl acrylate were added dropwise to a mixture of 16.8 g of propargyl alcohol and 0.1 g of sodium methoxide maintained at 55°-60° C. The mixture was then heated at 80° C. for 4 hours, after which it was left to stand overnight. The mixture was then poured into ice-water and extracted with ethyl acetate. The extract was dried and then purified by distillation to give 25.8 g of methyl β-propargyloxypropionate, boiling at 80°-83° C./10 mmHg.

Infrared absorption spectrum (liquid film) $\nu_{max}$ cm$^{-1}$: 3300, 2120, 1740.

3.2 g of the methyl β-propargyloxypropionate prepared as described above were suspended in 30 ml of water. 5.7 g of iodine and 5 ml of an aqueous solution containing 3 g of 85% w/w potassium hydroxide were simultaneously added dropwise at 0°-5° C. The mixture was then stirred at that temperature for 3 hours, after which a further 5.7 g of iodine were added and the mixture was stirred at room temperature for 3 hours. It was then left to stand overnight, after which the mixture was acidified with hydrochloric acid and extracted with ethyl acetate. The extract was dried and the solvent was distilled off to give crystals which, on recrystallization from a mixture of ethyl acetate and hexane, afforded 5.35 g of β-(2,3,3-triiodoallyloxy)propionic acid, melting at 115°-117° C.

2.9 g of this β-(2,3,3-triiodoallyloxy)propionic acid were added to 4 g of thionyl chloride and heated until dissolved. The mixture was then stirred at room temperature for 1 hour, after which the excess thionyl chloride was distilled off under reduced pressure. The resulting acid chloride was then added to 10 ml of ethanol and the mixture was stirred for 2 hours. The solvent was distilled off and the resulting residue was purified by column chromatography through silica gel eluted with a 3:1 by volume mixture of hexane and ethyl acetate to give 1.7 g of the desired Compound No. 101 in the form of an oil.

Elemental Analysis:
Calculated for $C_8H_{11}I_3O_3$: C, 17.93%; H, 2.07%; I, 71.04%. Found: C, 18.19%; H, 2.18%; I, 70.83%.

Infrared absorption spectrum (liquid film) $\nu_{max}$ cm$^{-1}$: 1740.

Rf value (thin layer chromatography on silica gel developed with a 3:1 by volume mixture of hexane and ethyl acetate): 0.54.

Following the procedure described in Examples 6 to 9, the compounds shown in the following Table 8 were prepared. Where the compounds were prepared in the form of crystals, their melting points are given; where they were prepared in the form of oils, this is stated and the Rf value is given (thin layer chromatography on silica gel developed with a 3:1 by volume mixture of hexane and ethyl acetate).

Also given are the corresponding properties of the compounds prepared in Examples 6-9.

TABLE 8

| Compound No. | Melting point (°C.) or Rf value | Infrared Absorption Spectrum (cm$^{-1}$) |
|---|---|---|
| 83 | 67–68 | 1735 |
| 84 | 73–74 | 1730 |
| 85 | 52–53 | 1730 |
| 87 | oil 0.65 | 1750 |
| 88 | 59–60 | 1750 |
| 89 | 62–63 | 1730 |
| 90 | 38–39 | 1730 |
| 91 | 85–86 | 1730 |
| 92 | 97–98 | 1730 |
| 93 | 70–71 | 1745 |
| 94 | oil 0.58 | 1770 |
| 95 | 112–113 | 1760 |
| 96 | oil 0.59 | 1760 |
| 97 | oil 0.59 | 1765 |
| 98 | oil 0.60 | 1760 |
| 99 | 99–100 | 1740 |
| 100 | 40–42 | 1740 |
| 101 | oil 0.54 | 1740 |
| 102 | oil 0.60 | 1735 |
| 103 | oil 0.64 | 1730 |
| 104 | oil 0.53 | 1740 |
| 105 | oil 0.51 | 1735 |

EXAMPLE 10

Emulsion 10 parts by weight of Compound No. 3 were dissolved in 40 parts of dimethylformamide. 50 parts of xylene and 10 parts of polyoxyethylene nonylphenyl ether were added to the solution and then the mixture was thoroughly blended to give an emulsion.

This emulsion may be diluted with any desired quantity of water and applied to wood or wood-based materials by various means, e.g. by coating, dipping or spraying. The emulsion can also be used, together with an adhesive, for the treatment of such materials as plywoods, particle boards or hardboards.

EXAMPLE 11

Oil-soluble preparation 2 parts by weight of Compound No. 28 were dissolved in 2 parts of dimethylformamide; 96 parts of solvent naphtha were then added to give an oil-soluble preparation. This preparation can be applied to wood and wood-based materials by such means as spraying, coating, dipping or impregnation.

EXAMPLE 12

Powder 2 parts by weight of Compound No. 1 were dissolved in 10 parts of acetone. 68 parts of clay and 30 parts of talc were then added to the solution and the mixture was thoroughly blended. The acetone was then vapourized to give a powder.

EXAMPLE 13

Wettable powder 40 parts by weight of Compound No. 27, 56 parts of clay, 3 parts of sodium lauryl sulphate and 1 part of polyvinyl alcohol were homogeneously blended in a mixer and then pulverized by a hammer mill to give a wettable powder.

EXAMPLE 14

Paint 10 parts by weight of Compound No. 28, 20 parts of barytes powder, 10 parts of vinyl resin, 25 parts of rosin and 35 parts of xylene were homogeneously blended to give a paint.

EXAMPLE 15

Aerosol 2 parts by weight of Compound No. 1 and 0.5 parts of a perfume were dissolved in 40 parts of deodorized kerosene. The resulting solution was charged into an aerosol vessel. After attaching a valve to the vessel, 58 parts of liquified petroleum gas were charged into it under pressure to give an aerosol.

EXAMPLE 16

Emulsion 10 parts by weight of Compound No. 84 were dissolved in 40 parts of dimethylformamide. 50 parts of xylene and 10 parts of polyoxyethylene nonylphenyl ether were added to the solution and then the mixture was thoroughly blended to give an emulsion. This emulsion can be used in the manner described in Example 10.

EXAMPLE 17

Oil-soluble preparation 2 parts by weight of Compound No. 83 were dissolved in 2 parts of dimethylformamide. 96 parts of solvent naphtha were then added to the solution to give an oil-soluble preparation, which can be used in the manner described in Example 11.

EXAMPLE 18

Powder 2 parts by weight of Compound No. 83 were dissolved in 10 parts of acetone. 68 parts of clay and 30 parts of talc were then added to the solution and the mixture was thoroughly blended. The acetone was then vapourized to give a powder.

EXAMPLE 19

Wettable powder 40 parts of Compound No. 85, 56 parts of clay, 3 parts of sodium lauryl sulphate and 1 part of polyvinyl alcohol were homogeneously blended in a mixer and then pulverized by a hammer mill to give a wettable powder.

EXAMPLE 20

Paint 10 parts of Compound No. 83, 20 parts of barytes powder, 10 parts of vinyl resin, 25 parts of rosin and 35 parts of xylene were homogeneously blended to give a paint.

EXAMPLE 21

Aerosol 2 parts by weight of Compound No. 84 and 0.5 part of a perfume were dissolved in 40 parts of deodorized kerosene. The resulting solution was charged into an aerosol vessel. After attaching a valve to the vessel, 58 parts of liquified petroleum gas were charged into it under pressure to give an aerosol.

EXAMPLE 22

Oil-based composition 0.1 part by weight of Compound No. 59 were dissolved in 99.9 parts of kerosene to give an oil-based composition.

EXAMPLE 23

Emulsifiable concentrate 90 parts by weight of Compound No. 39 were mixed with 5 parts of xylene and 5 parts of an emulsifier to give an emulsifiable concentrate, which is preferably diluted with water prior to application.

We claim:

1. An anti-fungal composition comprising an effective amount of an anti-fungal ingredient in admixture with a carrier or diluent, wherein the active ingredient is a compound of formula (Ia):

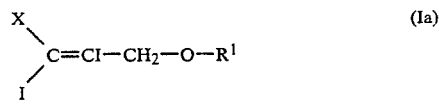

wherein:
X represents a bromine atom or an idine atom; and
$R^1$ represents an alkanoyl group having from 2 to 7 carbon atoms, a halogen-substituted alkanoyl group having from 2 to 4 carbon atoms, an alkoxycarbonyl group having from 2 to 6 carbon atoms, a halogen-substituted alkoxycarbonyl group having from 3 to 5 carbon atoms or an alkoxyalkoxycarbonyl group having a total of from 4 to 6 carbon atoms.

2. A composition as claimed in claim 1, wherein, in said active ingredient:
$R^1$ represents an alkanoyl group having from 2 to 4 carbon atoms or an alkoxycarbonyl group having from 2 to 4 carbon atoms.

3. The composition of claim 1 wherein said active ingredient is 3-acetoxy-1,1,2-triiodo-1-propene.

4. The composition of claim 1 wherein said active ingredient is 3-ethoxycarbonyloxy-1,1,2-triiodo-1-propene.

5. The composition of claim 1 wherein said active ingredient is 3-acetoxy-1-bromo-1,2-diiodo-1-propene.

6. The composition of claim 1 wherein said active ingredient is 3-ethoxycarbonyloxy-1-bromo-1,2-diiodo-1-propene.

7. Compounds of formula (Ia):

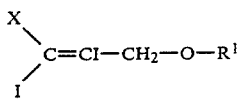 (Ia)

wherein:
X represents a bromine atom or an iodine atom; and
R¹ represents an alkanoyl group having from 2 to 7 carbon atoms, a halogen-substituted alkanoyl group having from 2 to 4 carbon atoms, an alkoxycarbonyl group having from 2 to 6 carbon atoms, a halogen-substituted alkoxycarbonyl group having 3 to 5 carbon atoms or an alkoxyalkoxycarbonyl group having a total of from 4 to 6 carbon atoms.

8. Compounds as claimed in claim 7, wherein R¹ represents an alkanoyl group having from 2 to 4 carbon atoms or an alkoxycarbonyl group having from 2 to 4 carbon atoms.

9. 3-Acetoxy-1,1,2-triiodo-1-propene.
10. 3-Ethoxycarbonyloxy-1,1,2-triiodo-1-propene.
11. 3-Acetoxy-1-bromo-1,2-diiodo-1-propene.
12. 3-Ethoxycarbonyloxy-1-bromo-1,2-diiodo-1-propene.

* * * * *